United States Patent
Kojima et al.

(10) Patent No.: US 6,777,683 B2
(45) Date of Patent: Aug. 17, 2004

(54) OPTICAL DETECTOR

(75) Inventors: Kennosuke Kojima, Kyoto (JP); Masahiko Ishida, Kyoto (JP); Shuji Takada, Kyoto (JP)

(73) Assignee: Horiba Ltd., Kyoto (JP)

( * ) Notice: Subject to any disclaimer, the term of this patent is extended or adjusted under 35 U.S.C. 154(b) by 222 days.

(21) Appl. No.: 10/072,960

(22) Filed: Feb. 12, 2002

(65) Prior Publication Data

US 2002/0122314 A1 Sep. 5, 2002

(30) Foreign Application Priority Data

Feb. 21, 2001 (JP) .................................... P. 2001-045570

(51) Int. Cl.⁷ .............................................. G01N 21/61
(52) U.S. Cl. .............................. 250/339.01; 250/338.1; 250/343
(58) Field of Search .................. 250/338.1, 339.01, 250/343, 336.1, 339.02; 356/432, 435

(56) References Cited

U.S. PATENT DOCUMENTS

| | | | |
|---|---|---|---|
| 3,860,344 A | | 1/1975 | Garfunkel |
| 4,560,875 A | | 12/1985 | Crowder |
| 5,493,123 A | * | 2/1996 | Knollenberg et al. ........ 250/372 |
| 5,796,472 A | * | 8/1998 | Wirthlin ...................... 356/72 |
| 5,914,489 A | * | 6/1999 | Baliga et al. ............ 250/339.05 |

FOREIGN PATENT DOCUMENTS

| | | |
|---|---|---|
| EP | 0 421 304 A1 | 4/1991 |
| JP | 08128895 | 5/1996 |
| WO | WO 97/25613 | 7/1997 |

* cited by examiner

Primary Examiner—John R. Lee
Assistant Examiner—Paul M. Gurzo
(74) Attorney, Agent, or Firm—Sughrue Mion, PLLC

(57) ABSTRACT

An optical detector 1 wherein detection elements 11, 12, 13 and 14 are provided in a sealed case 4 whose opening portion 3 is blocked with a window material 2 for transmitting light such as an infrared and an ultraviolet ray therethrough, the detection elements being formed opposite to the window material; and optical filters 21, 22, 23 and 34 are disposed between the window material 2 and the detection elements 11, 12, 13 and 14 and used for selecting and causing only light composed of a predetermined band of wavelengths to be transmitted by thin optical films in connection with the detection elements 11, 12, 13 and 14. The optical detector includes a shielding body 9 having housing portions 28, 29, 30 and 31 for containing the optical filters 21, 22, 23 and 24 and used for preventing any light composed of other than the predetermined band of wavelength selected by the thin optical films and preventing light producing an interference effect during measurement from being transmitted through the optical filters 21, 22, 23 and 24.

18 Claims, 5 Drawing Sheets

OPTICAL DETECTOR

The present invention relates to an optical detector in which optical filters are disposed between a window material for transmitting light such as an infrared and an ultraviolet ray and detection elements, each optical filter being corresponding to the each detection element. The optical filters are used for selecting and causing only light composed of a predetermined band of wavelengths to be transmitted by means of thin optical films in connection with the detection element.

There is an infrared-ray detector in which four optical filters respectively corresponding to four infrared-ray detection elements have substrates having the same thickness and while the edge faces of the substrates are set in the same plane and bonded together by an adhesive agent. The substrates are disposed in parallel integrally in the form of combined four squares in plan view. Each optical filter is obtained by dicing to scrape the substrate with a thin short-long cut portion and a band pass portion formed on the surface and undersurface. However, it has been impossible to completely prevent an infrared ray (hereinafter called infrared light) composed of other than the predetermined band of wavelengths selected by the short-long cut surface and the band pass surface as well as infrared light (disturbing light) producing an interference effect during measurement from being incident from the edge face (scraped face) of the optical filter thus obtained.

As shown in FIG. 7, for example, out of infrared light passing through an optical filter 70, the infrared light A' reflected in the optical filter 70 passes through an adhesive agent 77 from the edge face m (scraped face) of the optical filter 70 becomes incident from the edge face (scraped face) of an optical filter 72 adjacent to the optical filter 70. Further, the infrared light B' and C' reflected from the inner face 73a of the metal case 73 of an infrared-ray detector without passing through four optical filters including the optical filters 70 and 72 becomes incident on the optical filter 70 from the edge face (scraped face) m' of the optical filter 70, so that infrared light without passing on the short-long cut surface and/or the band pass surface produces such an interference effect.

SUMMARY OF THE INVENTION

An object of the present invention made in view of the foregoing circumstances is to provide an optical detector capable of shading disturbing light producing an interference effect.

In order to accomplish the object above, an optical detector according to the invention comprises a window material for transmitting light such as an infrared and an ultraviolet ray therethrough; a sealed case whose opening portion is blocked with said window material; detection elements being formed opposite to said window material in said sealed case; optical filters disposed between said window material and said detection elements, which transmits only light composed of a predetermined band of wavelengths by thin optical films, each optical filter corresponding to each detection elements; and a shielding body supporting said optical filters and preventing any light composed of other than the predetermined band of wavelength selected by said thin optical films and light producing an interference effect during measurement from being transmitted through said optical filters.

Further, in the optical detector, the shielding body includes housing portions for supporting said optical filters.

The invention provides an optical detector in which the surface of the shielding body is positioned higher than the surface of each of the optical filters.

According to the invention, the shielding body has an upper opening through which the light transmitted through the window material passes, a lower opening through which the light composed of the predetermined band of wavelength selected by the optical thin films after the light transmitted through the window material passes through the upper opening, and a filter receiving portion for mounting the optical filters as part of the undersurface of each of the optical filters makes contact with the filter receiving portion in the lower opening.

According to the invention, the shielding body is made of material, which absorbs the light, or the surface of the shielding body is processed by blackening for absorbing the light.

DETAILED DESCRIPTION OF THE PREFERRED EMBODIMENTS

Figure 1:
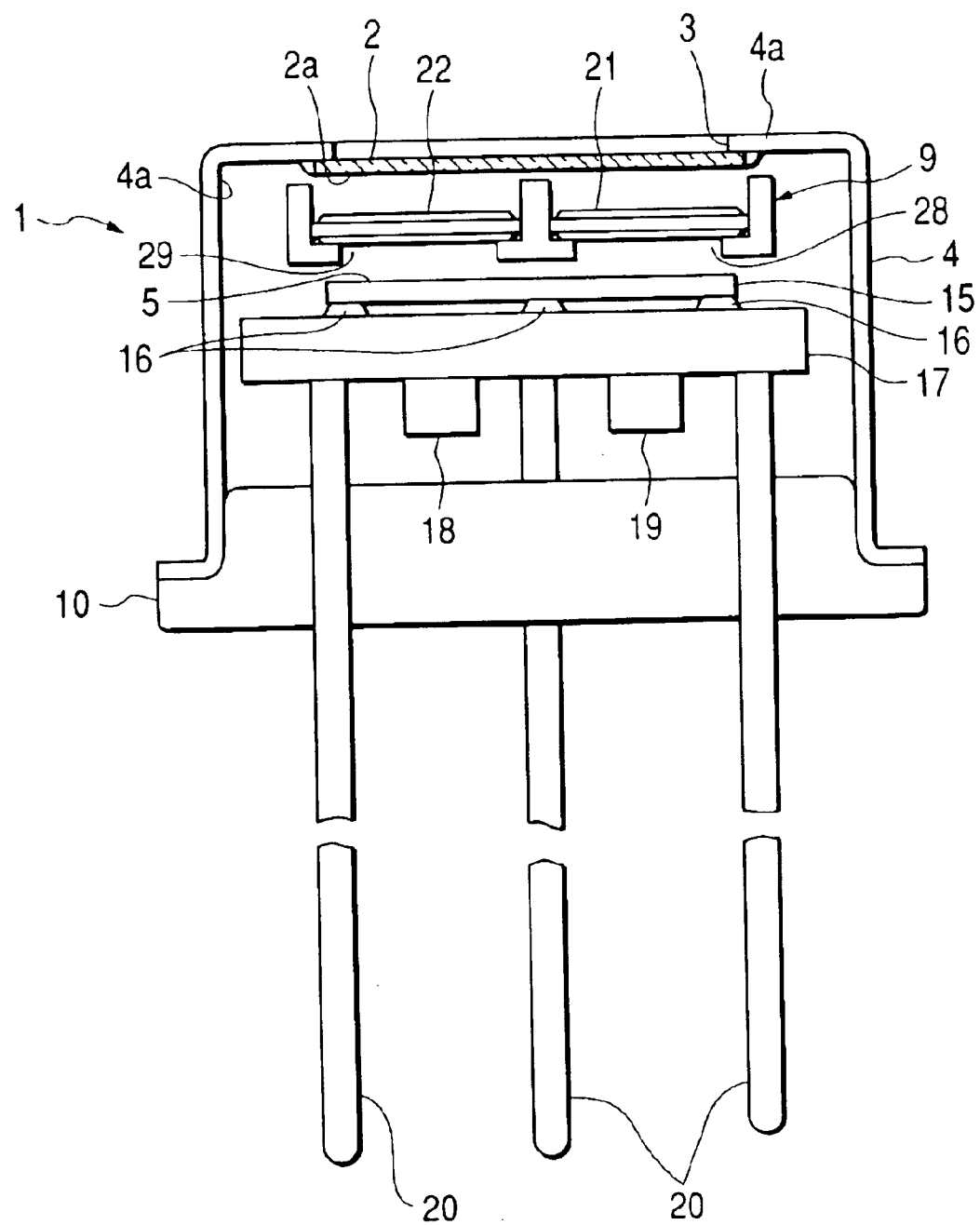
FIG. 1 is an overall diagram explanatory of the constitution of a first embodiment of the present invention.

A mode for carrying out the present invention will now be described with reference to the drawings.

FIGS. 1 to 4 shows a first embodiment of the invention wherein a shielding body for shading disturbing light producing an interference effect is provided between a plurality of infrared-ray detection elements and a window material; and an optical filter corresponding to each of the detection elements is contained in each housing portion of the shielding body.

In FIGS. 1 to 4, reference numeral 1 denotes an infrared-ray detector. The infrared-ray detector 1 essentially consists of a sealed case 4 whose opening portion 3 is blocked up with a window material 2 for transmitting infrared light, an infrared-ray detection element 5 provided opposite to the window material 2 in the sealed case 4, an optical filter 7 disposed between the window material 2 and the infrared-ray detection element 5 so that the optical filter 7 corresponds to the infrared-ray detection element 5, selects and causes only light composed of a predetermined band of wavelengths to be transmitted by means of an optical thin film, and a shielding body 9 for containing the optical filter 7 and preventing any light composed of other than the predetermined band of wavelengths selected by the optical thin film and infrared light producing an interference effect during measurement from being transmitted through the optical filter 7.

The sealed case 4 is formed of metal or the like and cylindrical in shape. Further, the opening portion 3 is provided on the end portion wall 4a of the sealed case 4. The window material 2 is made of sapphire, $CaF_2$, $SiO_2$ or the like. Reference numeral 10 denotes a stem for closing the case 4.

The infrared-ray detection element 5 is formed with four infrared-ray detection elements 11, 12, 13 and 14, for example, according to this embodiment of the invention. The infrared-ray detection elements 11, 12, 13 and 14 are formed on a pyroelectric element (e.g., PZT element) such that four electrode pairs consisting of four light receiving electrodes D, E, F and G and four compensating electrodes H, I, J and K respectively are positioned in point symmetry.

The pyroelectric element 15 is fixed to a circuit board 17 via a plurality of conductive spacers 16. Reference numeral 18 denotes a FET, 19 a high-resistance resistor forming part of an infrared circuit, and 20 lead terminals fitted through the stem 10 so as to support the circuit board 17 above the stem 10 with the space held therebetween.

According to this embodiment of the invention, the optical filter 7 is formed with four optical filters 21, 22, 23 and 24 corresponding to the respective infrared-ray detection elements 11, 12, 13 and 14.

The optical filter 21, for example, includes a substrate (e.g., an Si substrate) 25, a short-long cut surface 26 as an optical thin film formed on the surface of the substrate 25, and a band pass surface 27 as an optical thin film formed on the undersurface of the substrate 25. The short-long cut surface 26 functions as what cuts the short wavelength band and long wavelength band of infrared light, whereas the band pass surface 27 functions as what causes a predetermined wavelength band of infrared light corresponding to a measuring component to be transmitted. The other optical filters 22, 23 and 24 are also arranged in the same way.

Further, the shielding body 9 is made of material through which no infrared light passes and has four housing portions 28, 29, 30 and 31 corresponding to the number of optical filters 7.

Even though material through which infrared light passes is used for the shielding body 9, the invention is applicable to a shielding body having the surface processed by blackening whereby to absorb infrared light likewise.

Further, those having the same shape are employed as the respective optical filters 21, 22, 23 and 24 according to this embodiment of the invention and when the optical filters are square in plan view, for example, the four housing portions 28, 29, 30 and 31 are also made square in shape accordingly.

However, the invention is not limited to forming such squire optical filters 21, 22, 23 and 24 as shown in this embodiment thereof. Moreover, it is not necessarily needed to form all of the optical filters 21, 22, 23 and 24 in the same shape as in this embodiment of the invention.

Figure 2:
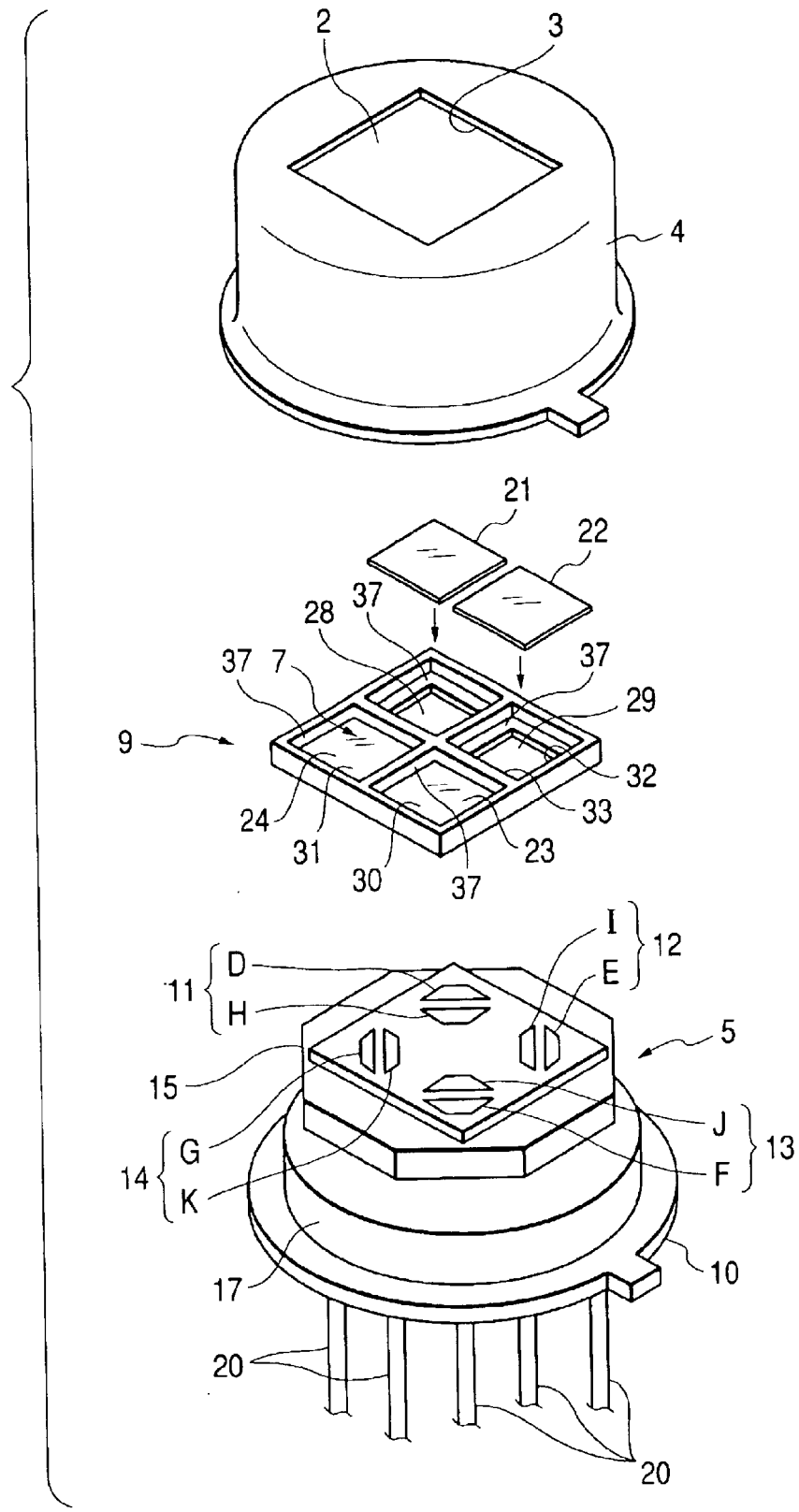
FIG. 2 is an exploded perspective view of the principal part of the above embodiment of the invention.
Figure 3A:
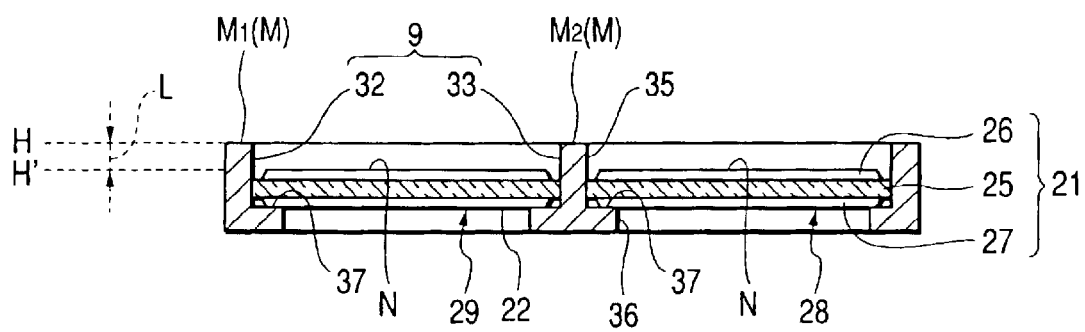
FIG. 3A is a diagram explanatory of a state in which optical filters are contained in a shielding body according to the above embodiment of the invention.
Figure 3B:
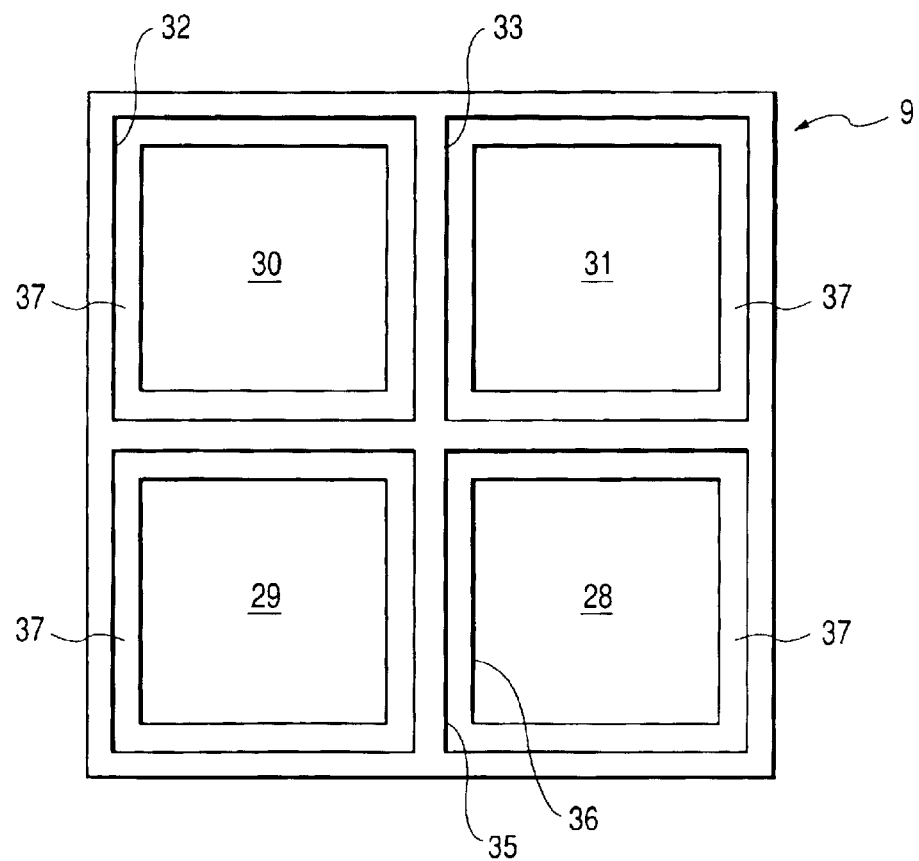
FIG. 3B is a plan view of the shielding body according to the above embodiment of the invention.

As shown in FIGS. 2 and 3, for example, the shielding body 9 is dish-shaped and formed like+ in plan view and the housing portions 28, 29, 30 and 31 are formed like a lattice frame so that the square optical filters 21, 22, 23 and 24 in plan view can be contained therein.

More specifically, the shielding body 9 is formed with an outer frame portion 32 in the form of+ in plan view and a partitioning portion 33 ranging in the form of+ in plan view. The outer frame portion 32 is square in plan view and L-shaped in vertical section, whereas the partitioning portion 33 is inverted-T-shaped in vertical section. The four housing portions 28, 29, 30 and 31 are formed by the outer frame portion 32 and the partitioning portion 33.

However, the invention is not limited to using the shielding body 9 in the form of+ in plan view when the plurality of optical filters are employed as in this embodiment thereof but may be arranged so that the optical filters are alternatively disposed depending on the optical system configuration including optical filters, the measuring component, the properties of the detection element (whether reference is needed or not) and so forth. Further, the disposition and shape of the shielding body 9 for simultaneously use as the housing portions 28, 29, 30 and 31 are needless to say made to follow changes in the disposition and shape of such optical filters.

The upper edge faces of the outer frame portion 32 and the partitioning portion 33 are set in the same plane. In other words, as shown in FIG. 3, the shielding body 9 is formed so that the upper edge face $M_1$ of the outer frame portion 32 and the upper edge face $M_2$ of the partitioning portion 33 are positioned (indicated by H) higher by a height of L than the positions (indicated by H') of the upper faces N of the optical filters 21, 22, 23 and 24. In this case, as the upper edge face of the shielding body 9 is composed of the upper edge faces $M_1$ and $M_2$, the upper edge face of the shielding body 9 is indicated by M hereinafter.

Figure 4:
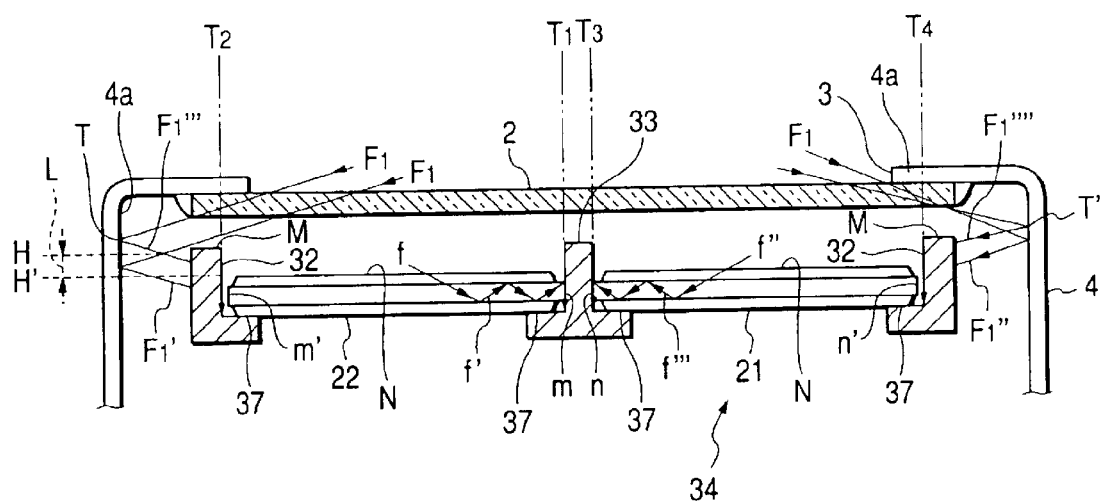
FIG. 4 is a diagram explanatory of the operation according to the above embodiment of the invention.

According to the invention, however, the upper edge faces of the outer frame portion 32 and the partitioning portion 33 are not necessarily needed to be set in the same plane. Moreover, the height L can be set at any given value to a certain degree. As shown in FIG. 4, for example, it is preferred to set the height of the shielding body 9 so that the light $F_1'''$ reflected at the point T of the inner face 4a of the metal case 4 and directed to the edge face (scraped face) m' of the optical filter 22 can also be shaded.

The shielding body 9 is fixed to the inner wall 4a of the case 4 or the undersurface 2a of the window material 2 by a proper means such as an adhesive agent (not shown).

The shielding body 9 in which the optical filter 21 is contained, for example, has a passage hole 34 in the housing portion 28, the infrared light transmitted through the window material 2 passing through the passage hole 34. The passage hole 34 has an upper opening 35 through which the infrared light transmitted through the window material 2 passes and a lower opening 36 through which the infrared light composed of the predetermined band of wavelengths selected by the short-long cut surface 26 as an optical thin film and by the band pass surface 27 passes, whereas each filter receiving portion 37 forming the lower opening 36 is formed in the housing portion 28. The size of the lower opening 36 is smaller than that of the upper opening 35 by what is equivalent to the filter receiving portion 37.

The filter receiving portion 37 is used to support the optical filter 21 inserted from above into the passage hole 34 and to mount the optical filter 21 in the housing portion 28 in such a condition that part of the underside of the optical filter 21 is kept in contact with the filter receiving portion 37. In this mounted condition, the upper edge face M of the shielding body 9 is positioned higher by L than the upper face N of the optical filter 21, which consequently dispenses with precision work for placing the four optical filters in the same plane as before, thus improving workability.

The filter receiving portion 37 is obtained by forming the L-shaped outer frame portion 32 in vertical section and the inverted-T-shaped partitioning portion 33 in vertical section.

According to this embodiment of the invention, the same filter receiving portion 37 in shape as the filter receiving portion 37 formed in the optical filter 21 is formed in the housing portions 29, 30 and 31 of the shielding body 9 in which the respective optical filters 22, 23 and 24 are contained.

Out of infrared light f passing through the optical filter 22, for example, the light f' reflected in the optical filter 22 can be shaded by the inverted-T-shaped partitioning portion 33 in vertical section from traveling from an edge face (scraped face) m toward the edge face (scraped face) n of the optical filter 21, for example, adjacent to the optical filter 22. Moreover, out of infrared light f" passing through the optical filter 21, the light f'" reflected in the optical filter 21 can be shaded by the inverted-T-shaped partitioning portion 33 in vertical section from traveling from an edge face (scraped face) n toward the edge face (scraped face) m of the optical filter 22.

Further, out of infrared rays $F_1$ that do not pass through any one of the optical filters 21, 22, 23 and 24, the light $F_1'$ reflected from the inner face 4a of the metal case 4 and traveling toward the edge face (scraped face) m' of the optical filter 22, for example, can be shaded by the L-shaped outer frame portion 32 in vertical section and the light $F_1''$ reflected from the inner face 4a and traveling toward the edge face (scraped face) n' of the optical filter 21, for example, can be shaded by the L-shaped outer frame portion 32 in vertical section.

As the upper edge face M of the L-shaped outer frame portion 32 in vertical section is positioned (indicated by H) higher by L, for example, than the position (indicated by H') of the surfaces N of the optical filters 21, 22, 23 and 24, moreover, the light $F_1'''$ reflected at the point T of the inner face 4a of the metal case 4 and directed to the edge face (scraped face) m' of the optical filter 22 can also be shaded. Similarly, the light $F_1''''$ reflected at the point T' of the inner face 4a of the metal case 4 and directed to the edge face (scraped face) n' of the optical filter 21 can also be shaded.

According to this embodiment of the invention, the housing portions 28, 29, 30 and 31 are provided by forming the shielding body 9 integrally with the L-shaped outer frame portion 32 in vertical section and the inverted-T-shaped partitioning portion 33 in vertical section, and the filter receiving portion 37 formed in the housing portions 28, 29, 30 and 31 is formed with the outer frame portion 32 and the partitioning portion 33. The advantage is that this arrangement is simultaneously usable as the shading function and the function of mounting the optical filters 22, 23 and 24 by means of the filter receiving portions 37 and that the shielding body 9 is easily built up.

According to this embodiment, further, in case where the edge faces m and m' of the edge face (scraped face) of the optical filter 22, for example, and the edge faces n and n' of the edge face (scraped face) of the optical filter 21, for example, are chipped off, the advantage is that disturbing light $T_1$, $T_2$, $T_3$ and $T_4$ caused and produced by the chipping (see FIG. 4) can be shaded by the filter receiving portion 37 formed in the inverted-T-shaped partitioning portion 33 in vertical section and the filter receiving portion 37 formed in the L-shaped outer frame portion 32 in vertical section.

Although there has been shown an example in which the outer frame portion 32 and the partitioning portion 33 are formed integrally according to this embodiment of the invention, the invention is also applicable to a case where both of the outer frame portion 32 and partitioning portion 33 are formed separately.

According to this embodiment of the invention, the shielding body 9 has been shown to have the housing portions 28, 29, 30 and 31 of the optical filters 21, 22, 23 and 24.

Figure 5:
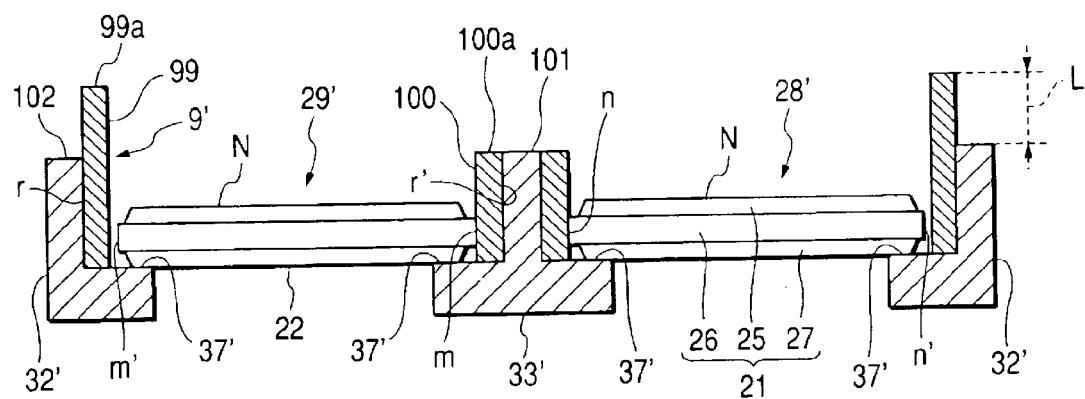
FIG. 5 is a diagram explanatory of the principal part according to a second embodiment of the invention.

FIG. 5 shows a second embodiment of the invention in which the housing portions 28', 29', 30' and 31' of optical filters 21, 22, 23 and 24 are separately formed from a shielding body 9', wherein like reference numerals and signs designate like and corresponding component parts shown in FIGS. 1 to 4.

Even in that case, the shielding body 9' is made of material through which no infrared light passes or even in case where material through which infrared light passes is used for the shielding body 9', the invention is applicable to a shielding body having the surface processed by blackening whereby to absorb infrared light likewise. Moreover, the housing portions 28', 29', 30' and 31' may be made of material through which infrared light passes. In FIG. 5, the housing portions 30' and 31' are not shown.

The housing portion 28' is formed with an L-shaped outer frame portion 32' in vertical section constituting a filter receiving portion 37' and an inverted-T-shaped partitioning portion 33' in vertical section constituting the filter receiving portion 37'. In addition, the housing portion 29' is also formed with the L-shaped outer frame portion 32' in vertical section and the inverted-T-shaped partitioning portion 33' in vertical section.

On the other hand, the shielding body 9' is integrally molded so as to contain the housing portions 28', 29', 30' and 31'. Of the shielding body 9' in this case, the surface 100a of a portion 100 supported by the partitioning portion 33' and the surface 101 of the partitioning portion 33' are set in the same plane. Moreover, the surface 102 of the outer frame portion 32' and the surface 101 of the partitioning portion 33' have the same height. Of the shielding body 9', further, the surface 99a of a portion 99 supported by the outer frame portion 32' is positioned higher by L than the surface 100a of the portion supported by the partitioning portion 33'. In other words, the surface 99a of the portion 99 of the shielding body 9' is positioned higher than the surfaces N of the optical filters 28' and 29'.

Although there have been shown examples in which the portion 99 of the shielding body 9' is held between the vertical face r of the outer frame portion 32' and the edge face (scraped face) m' of the optical filter 22 and in which the portion 100 of the shielding body 9' is held between the vertical face r' of the partitioning portion 33' and the edge face (scraped face) m of the optical filter 22, use may be made, as a shielding body, of a film with infrared-light absorbing material applied thereto, for example, so as to cover the whole peripheral face of the optical filter 22 including edge faces (scraped face) m' and m therewith and a shading film processed by blackening whereby to absorb infrared light. This is also the case with the optical filter 21.

Figure 6:
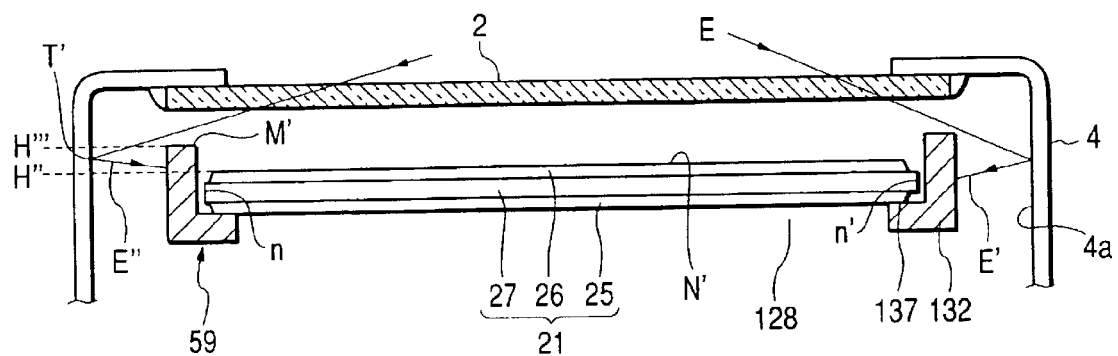
FIG. 6 is a diagram explanatory of the operating according to a their embodiment of the invention.
Figure 7:
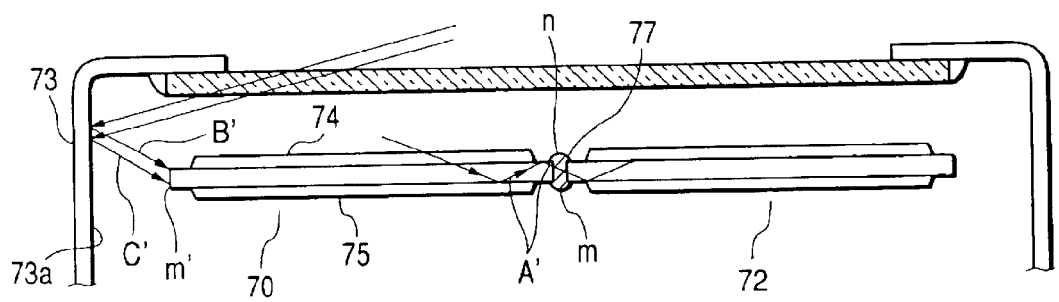
FIG. 7 is a diagram explanatory of the principal part of a conventional example.

FIG. 6 shows a third embodiment of the invention wherein a shielding body having only one housing portion for containing one optical filter is provided between an infrared-ray detection element and a window material so as to shade disturbing light producing an interference effect. In FIG. 6, like reference numerals and signs designate like and corresponding component parts shown in FIGS. 1 to 5.

In the third embodiment of the invention which is different from the first embodiment thereof, a shielding body 59 is formed with only an L-shaped outer frame portion 132 in vertical section forming a filter receiving portion 137. As in the first embodiment of the invention, the shielding body 59 is used simultaneously as the housing portion 128 of the optical filter 21 and thereby this arrangement is simultaneously usable as the shading function and the function of mounting the optical filter by means of the filter receiving portion 137, the advantage being that the shielding body 59 is easily built up.

As the shielding body 59 is arranged according to this embodiment of the invention so that the upper edge face M' of the shielding body 59, that is, the upper edge face M' of the outer frame portion 132 is positioned (indicated by H''') higher than the position (indicated by H'') of the surface N' of the optical filter 21, infrared light E that is transmitted through the window material 2 in an outer oblique direction but does not pass through the optical filter 21 is reflected from the inner face 4a of the metal case 4 and directed to the edge face (scraped face) n' of the optical filter 21 as reflected light E' can be shaded by the L-shaped outer frame portion 132 in vertical section. Moreover, infrared light E'' reflected at the point T' of the inner face 4a of the metal case 4 and directed to the edge face (scraped face) n of the optical filter 21 can also be shaded.

In this case, the housing portion 128 of the optical filter 21 may be formed separately from the shielding body 59.

This invention is applicable to a case where an ultraviolet-ray detector is used for measurement.

In the optical detector according to the invention, the detection elements are provided in the sealed case whose opening portion is blocked with the window material for transmitting light such as an infrared and an ultraviolet ray therethrough, the detection elements being formed opposite to the window material; and the optical filters are disposed between the window material and the detection elements and used for selecting and causing only light composed of a predetermined band of wavelengths to be transmitted by thin optical films in connection with the detection elements, the optical detector including a shielding body for containing the optical filters and preventing any light composed of other than the predetermined band of wavelength selected by the thin optical films and light producing an interference effect during measurement from being transmitted through the optical filters to ensure that the disturbing light producing the interference effect can be shaded.

What is claimed is:

1. An optical detector comprising:
   a window material for transmitting light such as an infrared and an ultraviolet ray therethrough;
   a sealed case whose opening portion is blocked with said window material;
   detection elements being formed opposite to said window material in said sealed case;
   optical filters disposed between said window material and said detection elements, which transmit only light composed of a predetermined band of wavelengths by thin optical films, each optical filter corresponding to each detection elements; and
   a shielding body supporting said optical filters and preventing any light composed of other than the predetermined band of wavelength selected by said thin optical films and light producing an interference effect during measurement from being transmitted through said optical filters.

2. An optical detector as claimed in claim 1, wherein said shielding body includes housing portions for supporting said optical filters.

3. An optical detector as claimed in claim 2, wherein a surface of said shielding body is positioned higher than a surface of each said optical filters.

4. An optical detector as claimed in claim 1, wherein a surface of said shielding body is positioned higher than a surface of each of said optical filters.

5. An optical detector as claimed in any one of claims 1 to 3, wherein said shielding body has an upper opening through which the light transmitted through said window material passes, a lower opening through which the light composed of the predetermined band of wavelength selected by said optical thin films after the light transmitted through said window material passes through said opening, and a filter receiving portion for mounting said optical filters makes contact with said filter receiving portion in said lower opening.

6. An optical detector as claimed in claim 5, wherein said shielding body is made of material which absorbs said light.

7. An optical detector as claimed in claim 5, wherein a surface of said shielding body is processed by blackening for absorbing said light.

8. An optical detector as claimed in any one of claims 1 to 3, wherein said shielding body is made of material which absorbs light.

9. An optical detector as claimed in any one of claim 1 to 3, wherein a surface of said shielding body is processed by blackening for absorbing light.

10. An optical detector as claimed in claim 1, wherein a surface of said shielding body is positioned higher than a top surface, of each of said optical filters, that is nearest the window material.

11. An optical detector comprising:
    a case having an opening portion;
    a window material for transmitting light therethrough, the window material disposed in the opening of the case;
    a detection element formed opposite to the window material in the case;
    an optical filter disposed between the window material and the detection element, the optical filter having an upper face facing the window material; and
    a shielding body supporting the optical filter, the shielding body comprising upper edge faces that define a recessed opening in which the optical filter is disposed, and the upper edge faces are positioned closer to the window material than is the upper face of the optical filter.

12. The optical detector according to claim 11, wherein the shielding body prevents the transmission of light reflected off an inside of the case from being incident on the optical filter and received by the detection element without first passing through the upper face of the optical filter.

13. The optical detector according to claim 11, further comprising a plurality of detection elements formed opposite to the window material in the case, and a plurality of optical filters disposed between the window material and the detection elements, the optical filters each having an upper face facing the window material;
    wherein each optical filter only transmits light composed of a respective predetermined band of wavelengths by thin optical films, each optical filter corresponding to one detection element; and
    wherein the shielding body includes a plurality of recessed openings in which the optical filters are supported, and the upper edge faces of the shielding body are positioned closer to the window material than are the upper faces of the optical filters.

14. The optical detector according to claim 13, wherein each recessed opening has an upper opening portion and a lower opening portion for allowing the transmission of light through the corresponding optical filter.

15. The optical detector according to claim 14, wherein the upper opening portion is larger than the lower opening portion.

16. The optical detector according to claim 13, wherein each pair of adjacent recessed openings are partitioned by a common wall member that is part of the shielding body and includes one of the upper edge faces, the common wall member preventing light from being transmitted between the pair of adjacent recessed openings.

17. The optical detector according to claim 11, wherein the case is a sealed case.

18. The optical detector according to claim 11, wherein the detection element is configured to detect an infrared or ultraviolet ray.

* * * * *